(12) United States Patent
Rioux et al.

(10) Patent No.: US 7,935,128 B2
(45) Date of Patent: May 3, 2011

(54) REMOTELY-RELOADABLE SUTURING DEVICE

(75) Inventors: Robert F. Rioux, Ashland, MA (US); David J. Sauvageau, Methuen, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1321 days.

(21) Appl. No.: 10/442,455

(22) Filed: May 21, 2003

(65) Prior Publication Data

US 2004/0236356 A1 Nov. 25, 2004

(51) Int. Cl.
*A61B 17/04* (2006.01)
*A61B 17/12* (2006.01)
(52) U.S. Cl. .......... 606/144; 606/148; 606/232
(58) Field of Classification Search .......... 606/150, 606/191–194, 139, 144–148, 232; 112/452, 112/169, 139
See application file for complete search history.

(56) References Cited

U.S. PATENT DOCUMENTS

| | | |
|---|---|---|
| 3,160,157 A | 12/1964 | Chisman |
| 3,840,017 A | 10/1974 | Violante |
| 3,946,740 A | 3/1976 | Bassett |
| 4,781,190 A | 11/1988 | Lee |
| 4,890,615 A | 1/1990 | Caspari et al. |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,935,027 A | 6/1990 | Yoon |
| 4,957,498 A | 9/1990 | Caspari et al. |
| 5,037,433 A | 8/1991 | Wilk et al. |
| 5,047,039 A | 9/1991 | Avant et al. |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |

(Continued)

FOREIGN PATENT DOCUMENTS

EP 1247492 A1 10/2002

(Continued)

OTHER PUBLICATIONS

Japanese Office Action with English Translation for related Japanese Patent Application No. 2006-533164. Dated Apr. 12, 2010, 7 pgs.

*Primary Examiner* — Gary Jackson
*Assistant Examiner* — Michael G Mendoza
(74) *Attorney, Agent, or Firm* — Brooks, Cameron & Huebsch, PLLC (57) ABSTRACT

A surgical instrument comprises an elongated body member having a distal end and a head extending from the distal end of the elongated body member, with the head comprising a remotely actuatable needle driver and a needle catch. A needle is adapted for receiving a suture and for being driven by the needle driver through a tissue into the needle catch, making a stitch. The instrument further comprises a remotely actuatable implement, such as a push bar, for moving the needle from a first position lodged in the needle catch to a second position dislodged from or able to be readily dislodged from the needle catch. The instrument may be used for placing multiple stitches without removing the instrument from the body. One particularly advantageous embodiment comprises a suturing device adapted for insertion in a body lumen, such as for attaching an endoluminal device to the lumen wall.

24 Claims, 8 Drawing Sheets

U.S. PATENT DOCUMENTS

| | | |
|---|---|---|
| 5,100,498 A | 3/1992 | Takeuchi et al. |
| 5,188,636 A | 2/1993 | Fedotov |
| 5,258,011 A | 11/1993 | Drews |
| 5,306,281 A | 4/1994 | Beurrier |
| 5,308,353 A | 5/1994 | Beurrier |
| 5,324,298 A | 6/1994 | Phillips et al. |
| 5,364,408 A | 11/1994 | Gordon |
| 5,387,221 A | 2/1995 | Bisgaard |
| 5,389,103 A | 2/1995 | Melzer et al. |
| 5,417,699 A | 5/1995 | Klein et al. |
| 5,458,609 A | 10/1995 | Gordon et al. |
| 5,527,321 A | 6/1996 | Hinchliffe |
| 5,540,704 A | 7/1996 | Gordon et al. |
| 5,545,171 A * | 8/1996 | Sharkey et al. ............... 606/148 |
| 5,562,686 A | 10/1996 | Sauer et al. |
| 5,573,542 A | 11/1996 | Stevens |
| 5,575,800 A | 11/1996 | Gordon |
| 5,578,044 A | 11/1996 | Gordon et al. |
| 5,662,664 A | 9/1997 | Gordon et al. |
| 5,700,272 A | 12/1997 | Gordon et al. |
| 5,713,910 A | 2/1998 | Gordon et al. |
| 5,741,277 A | 4/1998 | Gordon et al. |
| 5,741,279 A | 4/1998 | Gordon et al. |
| 6,048,351 A * | 4/2000 | Gordon et al. ............... 606/144 |
| 6,070,589 A | 6/2000 | Keith et al. |
| 6,096,051 A | 8/2000 | Kortenbach et al. |
| 6,197,035 B1 | 3/2001 | Loubens et al. |
| 6,346,111 B1 | 2/2002 | Gordon et al. |
| 6,368,334 B1 | 4/2002 | Sauer |
| 6,491,707 B2 | 12/2002 | Makower et al. |
| 6,533,795 B1 | 3/2003 | Tran et al. |
| 6,533,796 B1 | 3/2003 | Sauer et al. |

FOREIGN PATENT DOCUMENTS

| | | |
|---|---|---|
| WO | WO-9301750 | 2/1993 |

* cited by examiner

REMOTELY-RELOADABLE SUTURING DEVICE

TECHNICAL FIELD

This invention relates generally to endoscopic suturing devices, and, more specifically, to suturing devices capable of providing multiple stitches without removal from the body, and suturing devices capable of being used endoluminally.

BACKGROUND OF THE INVENTION

Endoscopic suture systems are well-known in the art, having been described in U.S. Pat. Nos. 5,364,408; 5,458,609; 5,540,704; 5,575,800; 5,578,044; 5,713,910; 6,048,351; and 6,346,111 B1 to Gordon et al., and U.S. Pat. No. 6,096,051 to Kortenbach et al., all of which are incorporated herein by reference and referred to collectively herein as "the Gordon and Kurtenbach patents." Commercial embodiments of these apparatus for placing sutures manufactured and sold by the assignee of the present invention are known in the art by the trademark CAPIO®. Other patents and commercial embodiments for endoscopic suturing are also known in the art.

Presently, these devices are capable of making a single stitch or "throw" inside the body, after which the device is retracted, and the suture is tied and cut, or the needle is reloaded in the device and the device returned to the body to place an additional stitch or "throw."

Endoluminal devices comprise the general category of devices that may be implanted in a body lumen, including but not limited to endoluminal prostheses, such as stents, grafts, and combinations thereof commonly referred to as stent-grafts; vena cava filters; and the like. Endoluminal devices may be implanted by so-called "minimally invasive techniques" in which the device, restrained in a radially compressed configuration, is delivered by a deployment system or "introducer" to the site where it is required. The introducer may enter the body through the patient's skin, or by a "cut down" technique in which the entry lumen, such as a blood vessel, is exposed by minor surgical means. When the deployment system has been navigated into the body lumen to the device deployment location, the system is manipulated to cause the endoluminal device to be expanded to a predetermined diameter at the deployment location, and the deployment system is withdrawn. As referred to herein, "proximal" refers to the direction closer to the end of the delivery system outside of the body lumen, and "distal" refers to the direction opposite the "proximal" direction.

It would be particularly advantageous to be able to place a device endoluminally with sutures to hold it in place. Because it is desirable to have more than one suture to hold a device in place, such as to secure a cylindrical prothesis against the walls of a body lumen, endoluminal suturing devices proposed for use in a body lumen may benefit from the ability to throw more than one stitch without having to withdraw the suturing device from the body between stitches. Thus, it is desirable to provide a remotely-reloadable suturing device that can be employed in a body lumen. Remote reloading, however, is desirable for any type of endoscopic suturing, not just endoluminal suturing.

SUMMARY OF THE INVENTION

One aspect of the invention comprises a surgical instrument comprising an elongated body member having a distal end and a head extending from the distal end of the elongated body member. The head defines a remotely actuatable needle driver and a needle catch; a needle adapted for receiving a suture and adapted to be driven by the needle driver through a tissue into the needle catch, making a stitch. The instrument further comprises a remotely actuatable implement, such as a push bar, for moving the needle from a first position lodged in the needle catch to a second position dislodged from or able to be readily dislodged from the needle catch.

The head may be adapted to rotate relative to the elongated body. The elongated body and head may be adapted for insertion in a body lumen. An endoluminal suturing device may have an inflatable balloon for stabilizing the head within a body lumen.

In one embodiment, the needle has a first diameter shoulder tapering to a pointed end and a body having a second diameter. The needle catch comprises a groove having a first width smaller than the first diameter of the needle shoulder, a neck portion having a second width narrower than the first width, and an opening having a diameter greater than the needle shoulder first diameter. The push bar may be adapted to move the needle in the needle catch from a first position in the groove on one side of the neck to a second position aligned with the opening on an other side of the neck.

The proximal end of the device may comprise a needle driver actuator for actuating a linkage to actuate the needle driver; a needle dislodgment actuator for actuating the implement for moving the needle from the first position in the needle catch to the second position, and; where the device comprises an inflatable balloon for stabilizing the head within a body lumen, a controller for controlling inflation of the balloon.

Another aspect of the invention comprises a surgical instrument comprising a flexible elongated body member; a head extending from the distal end of the elongated body member and comprising a remotely actuatable needle driver and a needle catch; and a needle adapted for receiving a suture and for being driven by the needle driver through a tissue into the needle catch to create a stitch. The elongated device and the head are adapted to be inserted in a body lumen and the elongated body comprises an inflatable balloon for stabilizing the head within a body lumen.

Another aspect of the invention comprises a method of making a running stitch with an endoscopic suturing device as described herein. The method comprises the sequential steps of connecting a suture to the needle and placing the needle in the needle driver; positioning the head in a first desired location adjacent a tissue; remotely actuating the needle driver to drive the needle through the tissue and into the needle catch to make a first stitch; and then remotely actuating the implement to move the needle from the first position lodged in the needle catch to the second position dislodged from or able to be readily dislodged from the needle catch. The needle is then completely dislodged from the needle catch and remotely reloaded into the needle driver, the head is positioned in another desired location; and the needle driver is remotely actuated to make another stitch. In an embodiment wherein the device is flexible and adapted to be introduced into a body lumen, the method further comprises inserting the device into a body lumen to reach the desired location. In an embodiment wherein the device comprises an inflatable balloon, and method further comprises inflating the balloon once the head is in a desired position to stabilize the head within the body lumen.

Still another aspect of the invention comprises a method of making a stitch with an endoscopic suturing instrument inside a body lumen, the instrument comprising a flexible elongated body member comprising an inflatable balloon, a head extending from the distal end of the elongated body member and comprising a remotely actuatable needle driver and a needle catch, and a needle. The method comprises the steps of connecting a suture to the needle and placing the needle in the needle driver; inserting the instrument into a body lumen and positioning the head in a desired location adjacent a portion of the lumen wall; inflating the balloon to stabilize the within the body lumen; remotely actuating the needle driver to drive the needle through the lumen wall and into the needle catch to create a stitch; and securing the stitch to the lumen wall.

In any of the various embodiments, at least the needle catch may be radiopaque, in which case the method of using the instrument may comprise using an imaging technique, such as computer tomography, to view the device as the method steps are performed.

The method of using the endoluminal suturing device may comprise securing an endoluminal device inside a body lumen. For example, for an endoluminal prosthesis comprising a stent having one or more apices, the methods may comprise securing the stent with one or more stitches, each stitch securing at least one apex to the lumen wall. In particular, the method may comprise securing the endoluminal prosthesis inside an aorta, such as to repair an abdominal aortic aneurysm.

In the endoluminal method in which the instrument comprises a remotely actuatable implement adapted to move the needle from a first position lodged in the needle catch to a second position dislodged from or able to be readily dislodged from the needle catch, the method may comprising creating a plurality of running stitches without removing the instrument from the body lumen.

It is to be understood that both the foregoing general description and the following detailed description are exemplary, but are not restrictive, of the invention.

BRIEF DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF INVENTION

The invention will next be illustrated with reference to the figures wherein similar numbers indicate the same elements in all figures. Such figures are intended to be illustrative rather than limiting and are included herewith to facilitate the explanation of the apparatus of the present invention.

Referring now to FIGS. 1-4, there is shown an exemplary surgical instrument 10 adapted for suturing from inside a body lumen 14. Instrument 10 comprises an elongated body member 16 having a head 18 at its distal end 20. Head 18, internal views of exemplary embodiments of which are shown in more detail in FIGS. 4 and 5A-5E, comprises a remotely actuatable needle driver 22 and a needle catch 24. A needle 26 adapted for receiving a suture 28 is adapted to be driven by needle driver 22 through tissue, such as through a lumen wall 12, and into needle catch 24, making a stitch 30.

Figure 1:
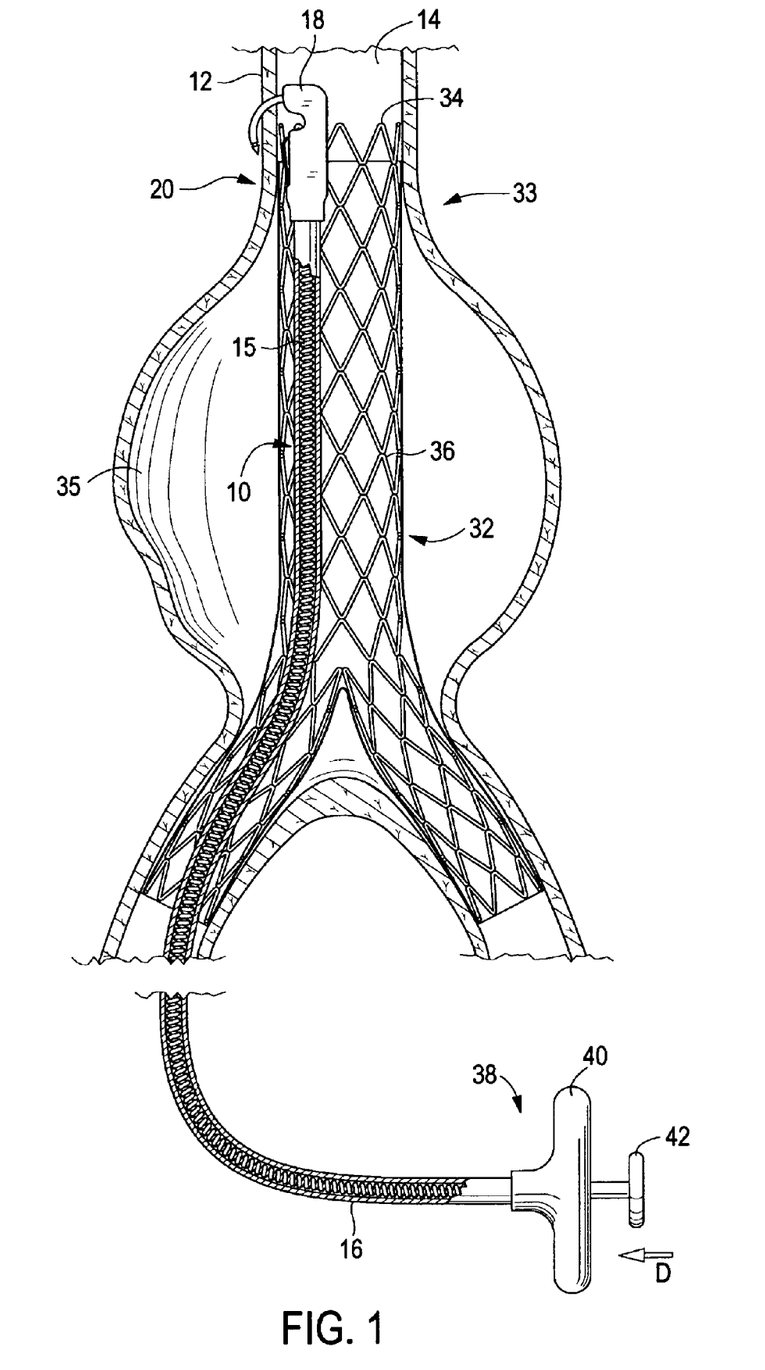
FIG. 1 depicts an abdominal aortic aneurysm (AAA) and endoluminal prosthesis in cross-section and a plan view of an exemplary endoluminal suturing device embodiment of the present invention in operation to suture the prosthesis to the body lumen.
Figure 2:
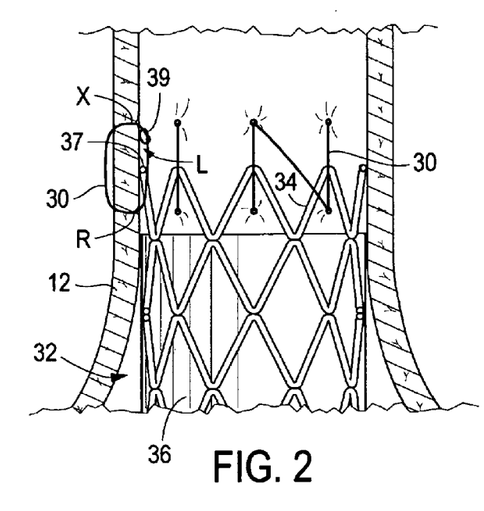
FIG. 2 shows a close up of a distal portion of the prosthesis of FIG. 1 after a suture has been placed.
Figure 3:
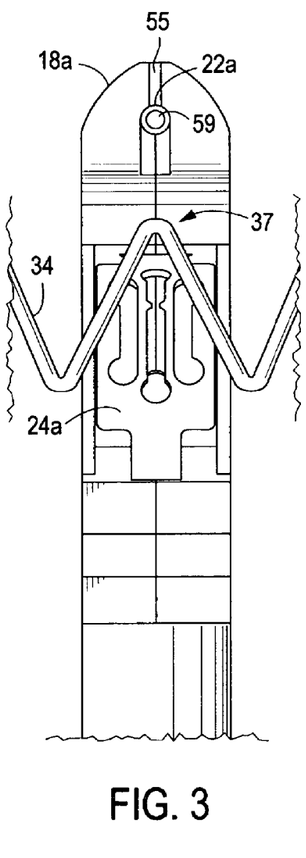
FIG. 3 shows a close-up of an exemplary head of the suturing device of FIG. 1 in a position to throw a suture, as viewed from the lumen wall.

As shown in FIGS. 1-3, instrument 10 may be used for securing an endoluminal device, such as an endoluminal prosthesis 32 to a lumen wall. Prosthesis 32 comprises a bifurcated device for implantation in an aorta 33, specifically for repairing an abdominal aortic aneurysm (AAA) 35. Prosthesis 32 comprises a stent 34 that protrudes distally from a graft lining or covering 36.

A T-shaped handle 40 and a plunger 42 are located at proximal end 38 of instrument 10. The T-shaped handle 40 is attached to elongated body 16. The plunger 42 is attached to shaft 44 (shown in FIG. 4) and spring coil 15 (shown in FIG. 1). The various elements shown in FIG. 1 and FIG. 4, and other elements not shown herein, operate generally as shown and described in U.S. Pat. Nos. 6,048,351 and 6,346,111, incorporated herein by reference. The novel features of the present invention, however, are not limited to application with respect only the embodiments shown and described in the '351 and '111 patents, but rather may be applied to any suturing devices known in the art, and particularly to any of the devices described in the Gordon and Kortenbach patents.

Figure 4:
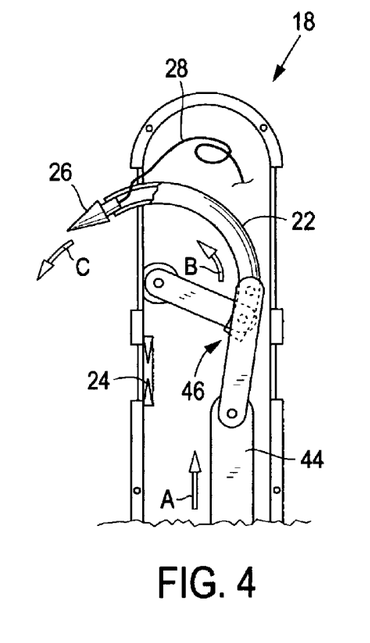
FIG. 4 shows an exemplary suturing head embodiment suitable for use in an endoluminal suturing device, having one portion of the outer casing removed to reveal an the needle driver, needle catch, shaft, and linkage for actuating the needle driver with the shaft.

Movement of plunger 42 in the direction of arrow D as shown in FIG. 1 causes shaft 44 to travel in the direction of arrow A, moving linkage 46 as indicated by arrow B in FIG.

4, causing needle driver 22 to actuate in the direction of arrow C. Although one type of linkage 46 is shown in FIG. 4, other linkages are known in the art, and the invention is not limited to any particular type of linkage or mechanism for remotely actuating needle driver 22. Actuation of needle driver 22 causes needle 26 to exit the lumen by piercing lumen wall 12 at an exit location X distal of apex 37 of stent 34 and to re-enter the lumen at a re-entry location R proximal of the stent apex as illustrated in FIG. 2, leaving stitch 30. In one embodiment, needle 26 sticks in needle catch 24, and instrument 10 is removed from the body so that the suture ends may be terminated in any way known in the art. For example, a knot 39 can be tied in the suture and advanced back through the lumen to location L adjacent the lumen wall 12, using an endoluminal knot pushing device known in the art (not shown), and loose ends of the suture can then be cut and removed, also as known in the art. U.S. Pat. No. 6,070,589, incorporated herein by reference, describes a number of exemplary methods and apparatus for terminating loose endoluminal suture ends. The invention is not limited, however, to any particular apparatus or methods for terminating the suture ends to secure stitches made using the present invention to the lumen wall.

Given the complications of having to remove the endoluminal device from the body for each stitch, it is particularly advantageous to provide a suturing instrument capable of throwing more than one stitch before needing to be removed. An exemplary embodiment of an instrument head 18a adapted to remotely reload the needle to allow multiple stitches without removing the device from the body is shown in FIGS. 3 and 5A-5E. In addition to having a needle catch 24a of a different geometry than needle catch 24 shown in FIG. 4, head 18a shown in FIGS. 5A-5E also comprises a remotely actuatable push bar 50 for moving the needle from a first position to a second position in the needle catch after it has been caught by the needle catch.

Figure 5A:
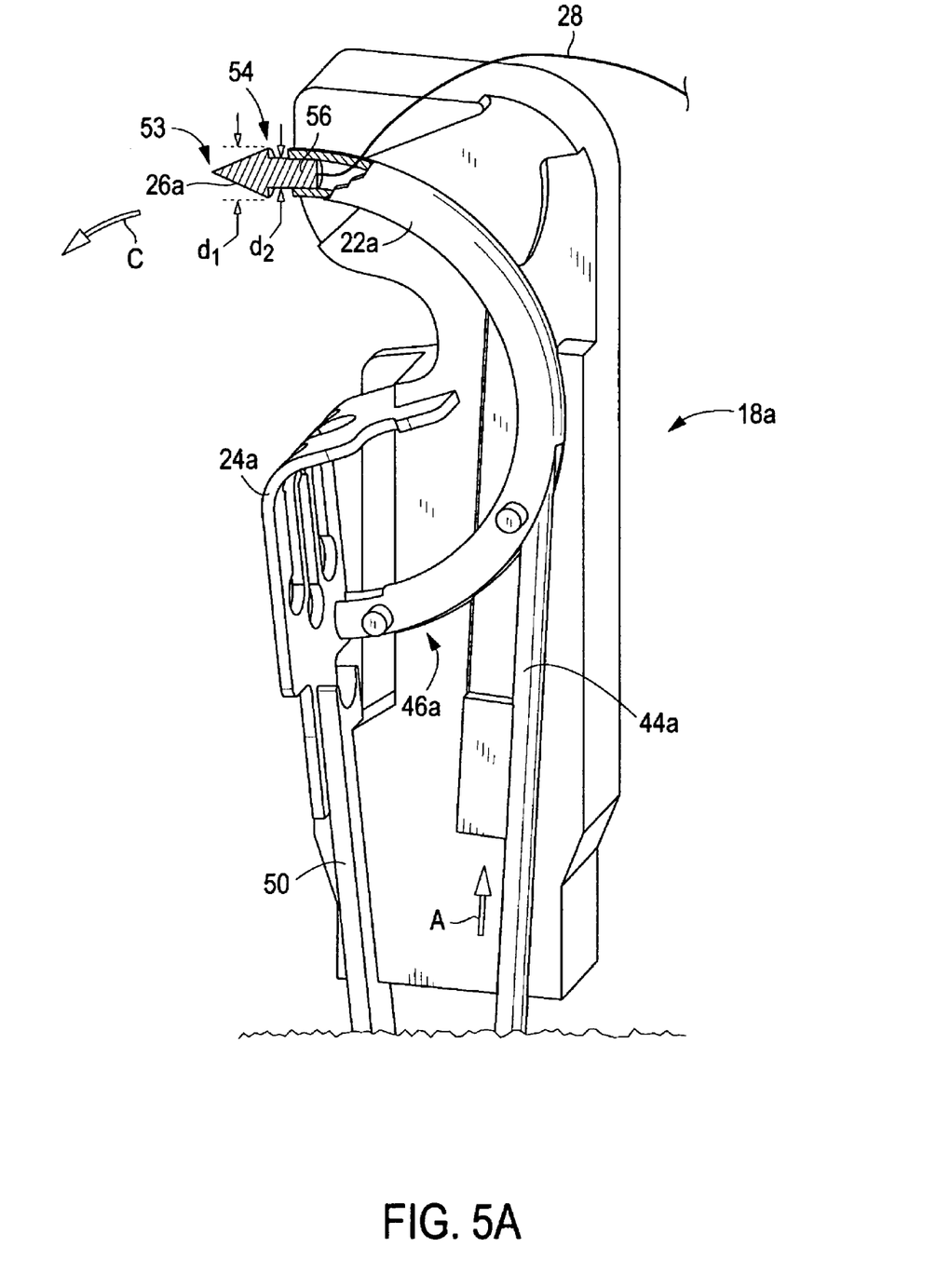
FIG. 5A shows an exemplary suturing head embodiment adapted for remotely reloading the needle driver with the needle, in a position before being actuated to place a first stitch.
Figure 5B:
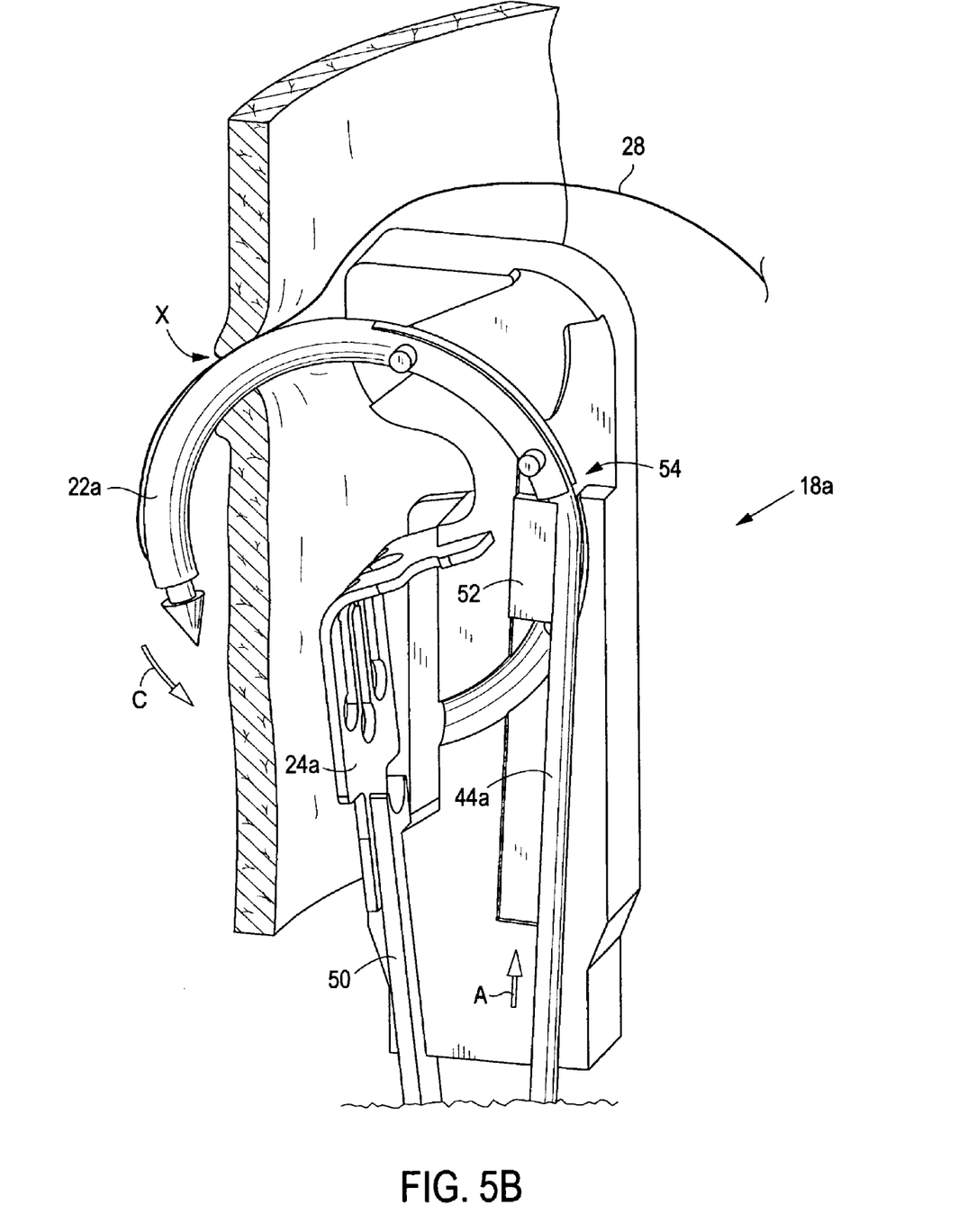
FIG. 5B shows the exemplary suturing head embodiment of FIG. 5A, in an intermediate position while being actuated to make a first stitch.

The operation of head 18a will now be described. First, as shown in FIG. 5A, suture 28 is received in needle 26a as is known in the art, and needle 26a is loaded into needle driver 22a. After head 18a has been positioned in a location where it is desired to throw one or more stitches, shaft 44a is remotely actuated as is known in the art to move in the direction of arrow A, such as by pushing a plunger 42 as indicated with respect to FIG. 1. Linkage 46a then translates the motion of shaft 44a into actuation of needle driver 22a in the direction of arrow C as shown in FIG. 5B. At an intermediate point, shown in FIG. 5B, block 52, connected to shaft 44a, engages the proximal end 54 of needle driver 22a to continue the translation of the motion of shaft 44a in the direction of arrow A into the motion of needle driver 22a in the direction of arrow C. As shown in FIG. 5B, the needle has already exited the lumen through lumen wall 12 at exit hole X.

Figure 5C:
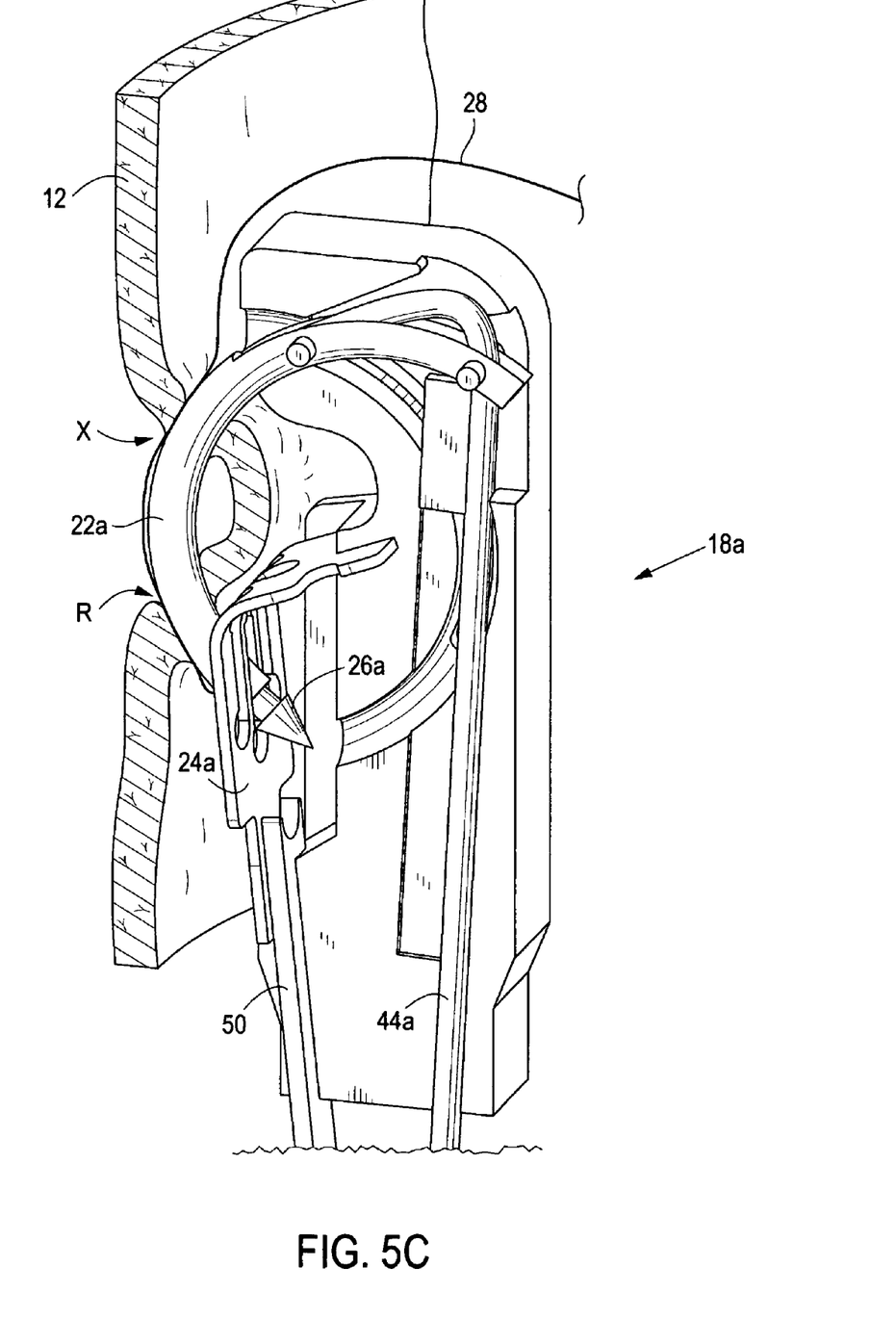
FIG. 5C shows the exemplary suturing head embodiment of FIG. 5B, in an fully actuated position in which the needle engages the needle catch.

At a fully actuated position, shown in FIG. 5C, needle driver 22a has re-entered the lumen by puncturing lumen wall 12 at re-entry hole R and needle 26a has engaged needle catch 24a. Shaft 44a and needle driver 22a are then returned to the position shown in FIG. 5D, with needle 26a remaining in needle catch 24a with suture 28 trailing behind it in a path extending through the lumen wall 12 via holes X and R.

Referring to FIG. 5A, needle 26a comprises a shoulder portion 54 having a first diameter $d_1$ that tapers to a pointed end 53, and a body 56 having a second diameter $d_2$ narrower than the shoulder portion. Referring now to FIGS. 6A-6C, there is shown a plan view of the interface between needle catch 24a, needle 26a, and push bar 50, as viewed from inside of head 18a along lines 6-6 shown in dashed lines in FIG. 5D. Needle catch 24a comprises a groove 60, defined by ribs 61a and 61b. Ribs 61a and 61b are preferably bounded by open area 63, so that the ribs are flexible enough to allow deformation when shoulder portion 54 of needle 26a pushes into groove 60. As shown in FIG. 6A, groove 60 has a first width $w_1$ that is smaller than diameter $d_2$ of shoulder portion 54 of needle 26a, and essentially the same or slightly smaller than diameter $d_3$ of body 56, so that groove 60 can hold needle 26a in place by frictional engagement between the walls of the groove and the body, while still allowing the body to move laterally in the groove. Neck portion 62 of groove 60 has a width $w_2$ smaller than width $w_1$ to create a portion where distal movement of needle 26a in the groove requires more applied force than in the rest of the groove. Opening 64 has a diameter $d_3$ that is greater than diameter $d_2$ of shoulder portion 54 of needle 26a.

Figure 5D:
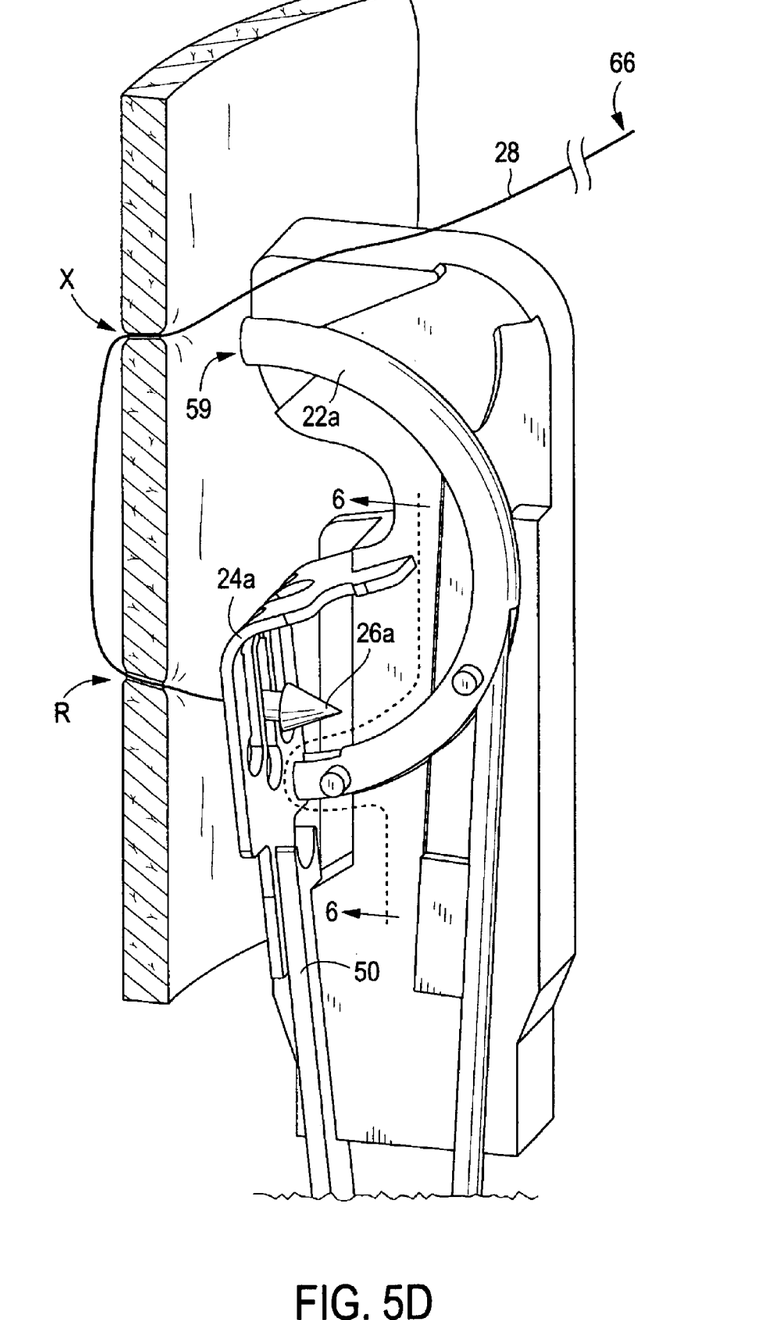
FIG. 5D shows the exemplary suturing head embodiment of FIG. 5C, with the needle in the needle catch and the needle driver returned to the unactuated position
Figure 5E:
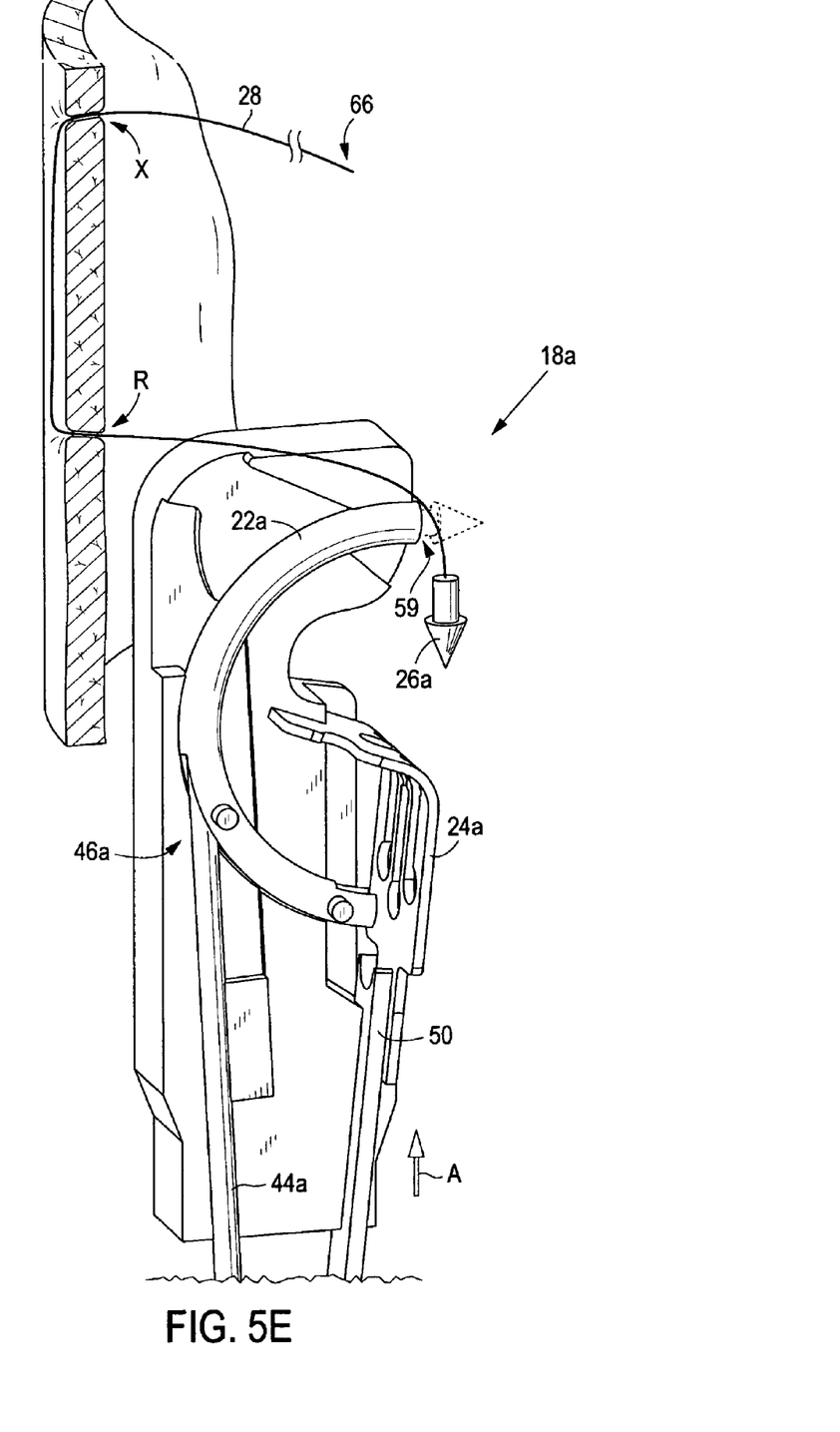
FIG. 5E shows the exemplary suturing head embodiment of FIG. 5D, in the process of the needle returning to the needle driver in preparation for making a second stitch.
Figure 6A:
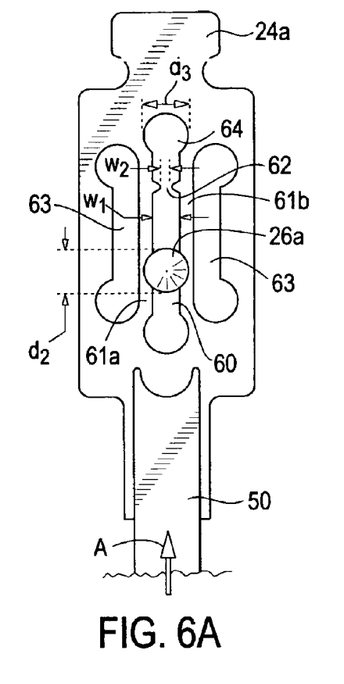
FIG. 6A shows an outward looking plan view of the push bar, needle catch, and needle shown in FIG. 5D as seen from inside the suturing device head along line 6-6.
Figure 6B:
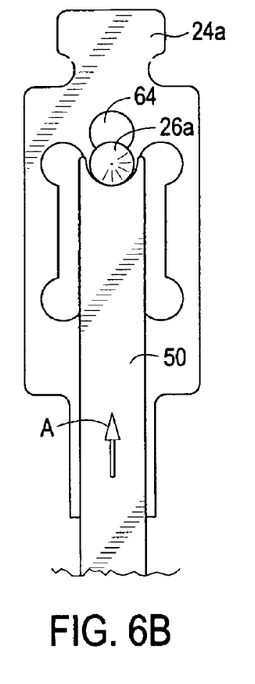
FIG. 6B shows the push bar, needle catch, and needle shown in FIG. 6A after the push bar has engaged the needle and pushed it beyond the neck portion of the needle catch groove.
Figure 6C:
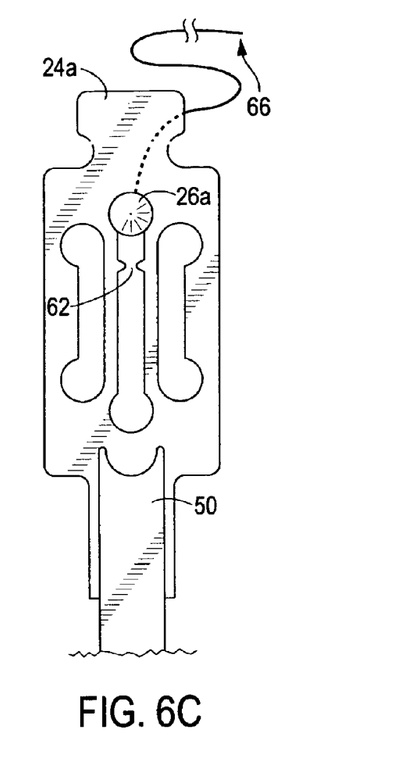
FIG. 6C shows the push bar, needle catch, and needle shown in FIG. 6B with the needle in the opening where it can be disengaged from the needle catch.

The position of needle 26a shown in FIG. 6A is essentially analogous to the position shown in FIG. 5D. Referring now to FIG. 5E, head 18a is now positioned so that exit portion 29 (the portion between re-entry hole R and needle 26a) of suture 28 is located in suture groove 55 (best illustrated in FIG. 3) along the top of needle driver 22a and suture 28 is held in tension. Although shown in FIG. 5E with head 18a rotated 180 degrees and lowered relative to the position shown in FIGS. 5A-5D, rotation, while helpful, is not necessary as long as suture 28 is engaged in suture groove 55. Push bar 50 is then advanced in the direction of arrow A to engage needle 26a as shown in FIG. 6B and to push the needle past neck portion 62 toward opening 64. Once needle 26a is aligned with opening 64, the opposite end 66 of suture 28 connected to needle 26a is pulled to free needle 26a from the needle catch 24a. Pulling on opposite end 66 of suture 28 causes needle 26a to follow the path of suture 28 through groove 55 along the top of needle driver 22a until the needle lodges in open end 59 of needle driver 22a in the same manner shown in FIG. 5A. After reloading needle 26a in needle driver 22a, suture 28 extends from its end 66 outside the body lumen, through exit hole X, through re-entry hole R, and into needle 26a loaded in needle driver 22a. Head 18a may now be rotated to whatever orientation desired to throw an additional stitch by repeating the process described above and shown in FIGS. 5A-5E. Once the desired number of stitches have been thrown, the suture ends may be terminated in any way known in the art, as discussed above.

Although described with respect to an endoluminal embodiment herein, it should be recognized that the auto-reloading head as shown in FIGS. 5A-6C may be beneficial for non-endoluminal applications as well. Accordingly, the push bar and needle catch arrangement shown in FIGS. 6A-6C may be provided on any type of suturing device known in the art. Also, the needle catch design is not limited to any particular geometry, but rather is characterized by any type of design that enables the needle to be manipulated remotely to undo the needle from the needle catch.

Figure 7:
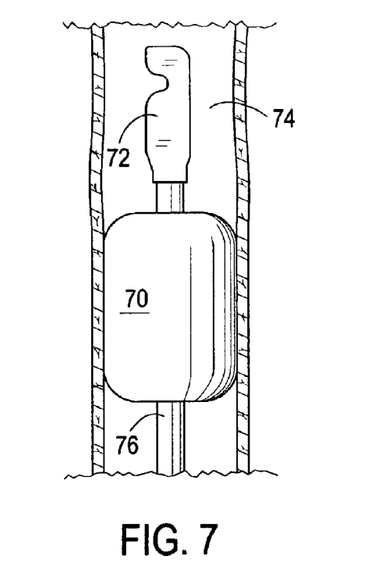
FIG. 7 shows a distal portion of an exemplary endoluminal suturing device of the present invention comprising a stabilizing balloon.

Additional features may be present to provide advantages in endoluminal applications. For example, as shown in FIG. 7, an inflatable balloon 70 may be provided to stabilize suturing head 72 within lumen 74. The fully inflated balloon may have a shape that completely blocks blood flow, if desired, or a shape which allows continued blood to flow past the balloon. Although inflation of the balloon may essentially center head 72 axially within lumen 74, the invention is not limited to applications in which the head is precisely centered. In one embodiment, elongated body member 76 may be rotatable relative to balloon 70, such as, for example, where balloon 70 comprises a sleeve over elongated body member 76. In another embodiment, head 72 may be rotatable relative to elongated body member 76.

With respect to an embodiment in which head 72 is rotatable relative to elongated body member 76, the range of rotation may have a plurality of, and preferably at least four, stops, each of which provide feedback to the user, such as an audible and/or tactile feedback, when the head has been seated in a stop. For example, the head may "click" into one or more locations across the range of rotation, providing such audible and tactile feedback, and requiring more force to rotate the head from the "clicked" location than across the rest of the range of motion. Suturing instruments having a rotatable head relative to the body are described generally in U.S. Pat. No. 6,048,351, to Gordon et al., incorporated herein by reference. In particular, it may be advantageous for the four spots to be 90 degrees apart from one another, giving the user the ability to reliably place four sutures, 90 degrees apart inside the lumen to attach the prosthesis or other endoluminal device to the lumen wall.

Figure 8:
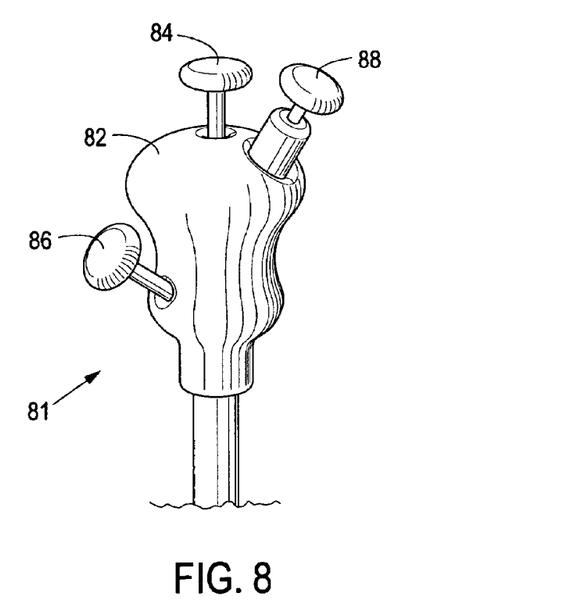
FIG. 8 shows an exemplary proximal portion of an exemplary endoluminal suturing device of the present invention having actuation means for the needle driver, push bar, and inflatable balloon.

Referring now to FIG. 8, there is shown an exemplary proximal end 81 of a suturing device comprising a balloon 70 as shown in FIG. 7 and a pushbar 50 as shown in FIGS. 5A-6C or other mechanism for providing in situ needle reloading. Proximal end 81 comprises a substantially T-shaped handle 82, a first plunger 84 for remotely actuating the needle driver, a second plunger 86 for remotely actuating the push bar, and a port 88 for injecting saline solution or other fluid for inflating balloon 70. It should be understood that an embodiment having a balloon but not push bar may have a similar appearance to the proximal end as shown in FIG. 8, absent the second plunger 86. Similarly, an embodiment having a push bar but no balloon, may have a similar appearance to the proximal end shown in FIG. 8 absent port 88. An embodiment having neither a balloon or a push bar has an appearance as shown in FIG. 1.

The materials of construction for embodiments of this invention may be any materials known in the art for medical devices. In one embodiment, elongated body 16 comprises a spring casing wrapped with heat shrink tubing. In another embodiment, one or more elements of the instrument, in particular at least the needle catch, may be radiopaque. In this way, imaging techniques, such as but not limited to computed tomography (CT), may be used to view the device continuously or periodically while the method steps are being performed. In instruments adapted for reloading inside the body, providing the needle catch, the needle, and the needle driver all with radiopacity to some degree, may provide visual verification to the user that the needle has been reloaded.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention.

What is claimed:

1. A surgical instrument, comprising:
   an elongated body member having a distal end;
   a head extending from the distal end of the elongated body member, the head comprising a remotely actuatable needle driver and a needle catch;
   a needle configured for receiving a suture and for being driven by the needle driver through a tissue into the needle catch to create a first stitch; and
   a remotely actuatable implement for moving the needle from a first position lodged in the needle catch to a second position dislodged from, or able to be readily dislodged from, the needle catch comprising a needle driver actuator at a proximal end of the device for actuating a linkage to actuate the needle driver and a needle dislodgment actuator for actuating the implement for moving the needle from the first position in the needle catch to the second position, wherein the needle is configured to remotely reload into the needle drive to create a second stitch through the tissue while remaining within a body of a patient.

2. The surgical instrument of claim 1, wherein the head is configured to rotate relative to the elongated body.

3. The surgical instrument of claim 2, wherein the head has a plurality of rotational positions.

4. The surgical instrument of claim 3, wherein the head clicks into each of the plurality of rotational positions to provide feedback to a user of the surgical instrument.

5. The surgical instrument of claim 4, wherein the feedback is tactile.

6. The surgical instrument of claim 4, wherein the feedback is audible.

7. The surgical instrument of claim 2, wherein the implement for moving the needle from the first position in the needle catch to the second position comprises a pushbar.

8. The surgical instrument of claim 7, wherein the needle has a first diameter shoulder tapering to a pointed end and a body having a second diameter, and the needle catch comprises a groove having a first width smaller than the first diameter of the needle shoulder, a neck portion having a second width narrower than the first width, and an opening having a diameter greater than the needle shoulder first diameter.

9. The surgical instrument of claim 8, wherein the push bar is adapted to move the needle in the needle catch from the first position in the groove on one side of the neck to the second position aligned with the opening, on an other side of the neck.

10. The surgical instrument of claim 9, wherein the elongated body and head are configured for insertion in a body lumen and the instrument further comprises:
    an inflatable balloon for centering the head within a body lumen; and
    a controller at the proximal end of the instrument for controlling inflation of the balloon.

11. The surgical instrument of claim 1, wherein the elongated body is flexible.

12. The surgical instrument of claim 1, wherein the elongated body and head are configured for insertion in a body lumen.

13. The surgical instrument of claim 12 further comprising an inflatable balloon for stabilizing the head within a body lumen.

14. The surgical instrument of claim 13, wherein the inflatable balloon is positioned proximally of the head.

15. The surgical instrument of claim 13, wherein the head is rotatable relative to the inflatable balloon.

16. The surgical instrument of claim 13, wherein the inflatable balloon is positioned on a sleeve that is rotationally independent of the elongated body.

17. The surgical instrument of claim 12, wherein the elongated device and the head are configured to be inserted into a vascular lumen.

18. The surgical instrument of claim 1, wherein the needle driver actuator is connected to the needle driver by a flexible shaft.

19. The surgical instrument of claim 1, wherein the elongated body comprises a T-shaped handle at its proximal end and the needle driver actuator comprises a plunger that interfaces with the T-shaped handle.

20. The surgical instrument of claim 1, wherein the elongated body comprises a spring casing wrapped with heat shrink tubing.

21. The surgical instrument of claim 1, wherein the needle catch is radiopaque.

22. A surgical instrument, comprising:
- a flexible elongated body member having a distal end;
- a head extending from the distal end of the elongated body member, the head comprising a remotely actuatable needle driver and a needle catch;
- a needle configured for receiving a suture and for being driven by the needle driver through a tissue into the needle catch, making a stitch; and
- a remotely actuatable implement for moving the needle from a first position lodged in the needle catch to a second position dislodged from or able to be readily dislodged from, the needle catch comprising a needle driver actuator at proximal end of the device for actuating a linkage to actuate the needle driver and a needle dislodgment actuator for actuating the implement for moving the needle from the first position in the needle catch to the second position, wherein the needle is configured to remotely reload into the needle drive to create a second stitch through the tissue while remaining within a body of a patient;
- wherein the elongated device and the head are configured to be inserted in a body lumen and the elongated body comprises an inflatable balloon for stabilizing the head within the body lumen.

23. The surgical instrument of claim 22, wherein the inflatable balloon is positioned proximally of the head.

24. The surgical instrument of claim 22, further comprising at a proximal end of the device:
- a needle driver actuator for actuating a linkage to actuate the needle driver; and
- a controller at the proximal end of the instrument for controlling inflation of the balloon.

* * * * *